United States Patent
Wang

(10) Patent No.: US 10,893,969 B2
(45) Date of Patent: Jan. 19, 2021

(54) REAR SHEET ADJUSTMENT ASSEMBLY OF NECK COLLAR

(71) Applicant: Meng-Chun Wang, Taichung (TW)

(72) Inventor: Meng-Chun Wang, Taichung (TW)

( * ) Notice: Subject to any disclaimer, the term of this patent is extended or adjusted under 35 U.S.C. 154(b) by 471 days.

(21) Appl. No.: 15/970,051

(22) Filed: May 3, 2018

(65) Prior Publication Data
US 2019/0336316 A1    Nov. 7, 2019

(51) Int. Cl.
*A61F 5/055* (2006.01)

(52) U.S. Cl.
CPC .................... *A61F 5/055* (2013.01)

(58) Field of Classification Search
CPC .... A61F 5/055; A61F 5/01; A61F 5/05; A61F 5/37; A61F 5/05883; A61F 5/05833; A61F 5/05816; A61F 5/3707; A61F 13/12; A61F 13/128
USPC .................... 602/5, 17–18; 128/869, DIG. 23
See application file for complete search history.

(56) References Cited

U.S. PATENT DOCUMENTS

| | | | | |
|---|---|---|---|---|
| 5,593,382 A | * | 1/1997 | Rudy, Jr. | A61F 5/055 602/18 |
| 7,041,073 B1 | * | 5/2006 | Patron | A61F 5/055 602/17 |
| 2012/0165712 A1 | * | 6/2012 | Calabrese | A61F 5/055 602/18 |

FOREIGN PATENT DOCUMENTS

TW         D159021 S      2/2014

* cited by examiner

*Primary Examiner* — Rachael E Bredefeld
*Assistant Examiner* — Caitlin A Carreiro
(74) *Attorney, Agent, or Firm* — Muncy, Geissler, Olds and Lowe, P.C.

(57) ABSTRACT

A rear sheet adjustment assembly of neck collar is provided, including a nape base and a support sheet. The nape base includes a main body, at least one stopper, a positioning member and a plurality of openings. The at least one stopper is connected with the main body and defines an inserting space therebetween. The positioning member is disposed on the main body. The positioning member has a first combination portion. The support sheet is adapted for supporting a nape of a neck and movably inserted within the inserting space. The support sheet has a plurality of second combination portions, and each of the second combination portions is adjustably engageable with the first combination portion.

7 Claims, 8 Drawing Sheets

REAR SHEET ADJUSTMENT ASSEMBLY OF NECK COLLAR

BACKGROUND OF THE INVENTION

Field of the Invention

The present invention relates to a neck protection device, especially a rear sheet adjustment assembly of neck collar.

Description of the Prior Art

Neck is one of the most important parts of human body and also a part constantly to be moved. Once the neck is injured, it is easily to get injured again due to unexpected head and neck activities, which results in slow recovery. A neck protection device is developed to improve this phenomenon. The neck protection device is able to cover around the neck of a patient to support and restrict actions of the head and neck so as to avoid the neck getting injured again. The neck protection device disclosed in TWD159021 is the type described above.

Most commercial neck protection devices focus on improvement in materials, so that the users may feel comfortable when wearing it or may not have adverse reactions when wearing for a long time. However, the commercial neck protection devices lack for the firmness and stability in wearing, which needs to be improved.

The present invention is, therefore, arisen to obviate or at least mitigate the above-mentioned disadvantages.

SUMMARY OF THE INVENTION

The main object of the present invention is to provide a rear sheet adjustment assembly of neck collar. A support sheet is adjustable to be suitable for the neck of different users and can stably support and protect the neck so as to prevent the neck from getting injured.

To achieve the above and other objects, the present invention provides a rear sheet adjustment assembly of neck collar, including: a nape base and a support sheet. The nape base includes a main body, at least one stopper, a positioning member and a plurality of openings. The at least one stopper is connected with the main body and defines a first distance and an inserting space therebetween. The positioning member and the at least one stopper is disposed oppositely on the main body, and at least part of the positioning member is movable to a blocking position and a releasing position. A first combination portion of the positioning member is insertable into the inserting space, and each of the openings is configured for a band to be disposed therethrough. The support sheet is configured to support a nape and is movably inserted within the inserting space. The support sheet includes a plurality of second combination portions, and each of the second combination portions is adjustably engageable with the first combination portion. Wherein the first combination portion is located at the inserting space and engaged with one of the second combination portions when the positioning member is in the blocking position; the first combination portion is departed from the second combination portions and moved away from the support sheet when the positioning member is in the releasing position.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
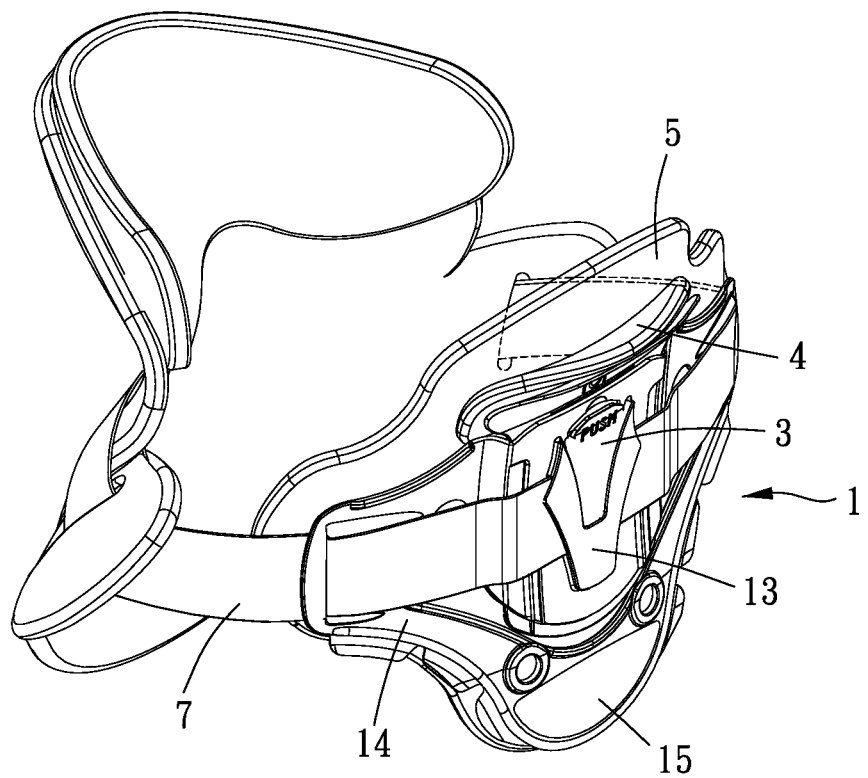
FIG. 1 is a stereogram of a preferable embodiment of the present invention in use.
Figure 2:
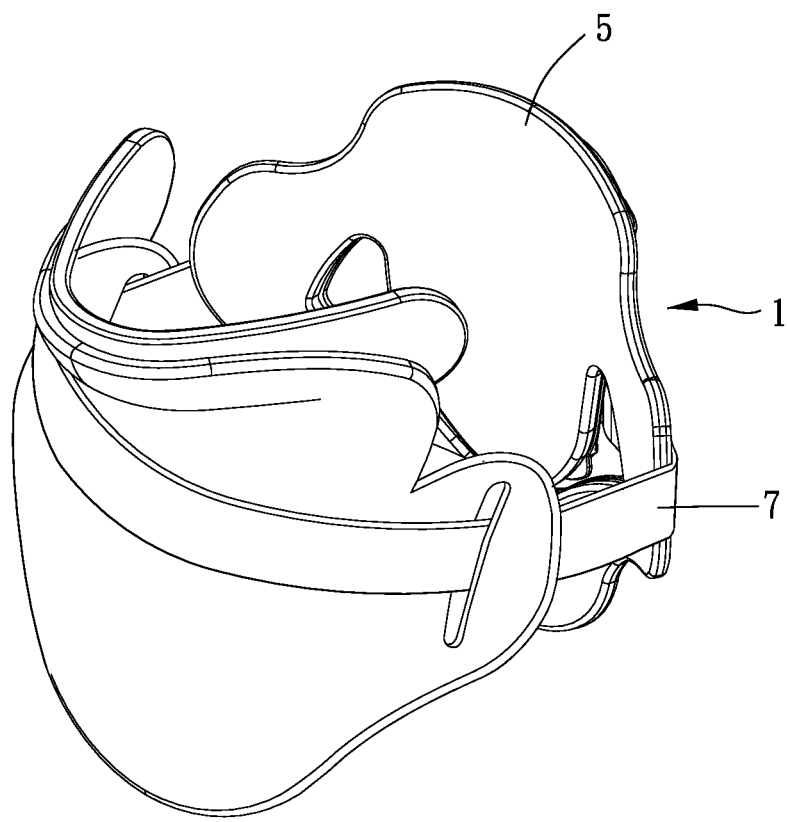
FIG. 2 is a stereogram of FIG. 1 at another viewpoint.
Figure 3:
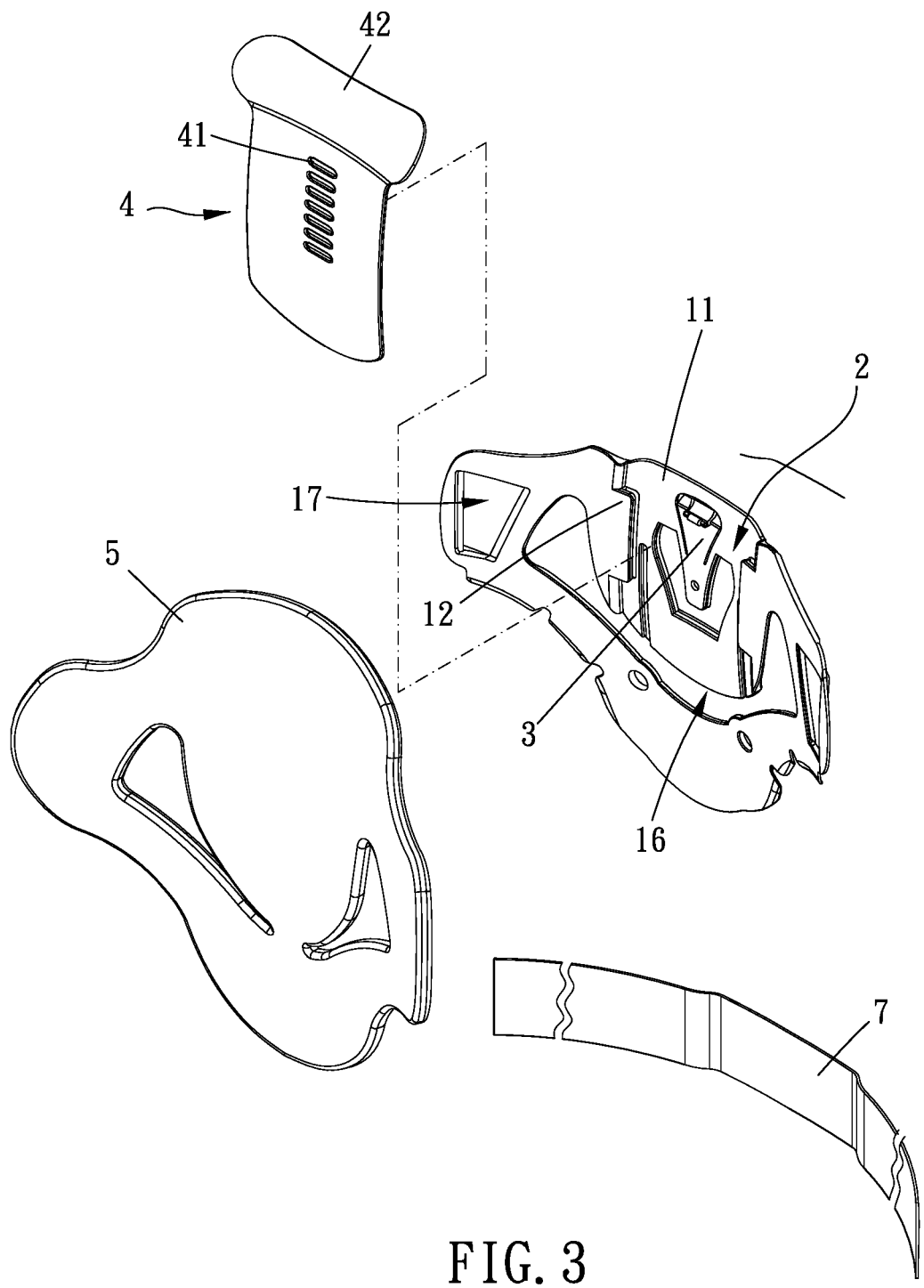
FIG. 3 is a breakdown drawing of a preferable embodiment of the present invention.
Figure 4:
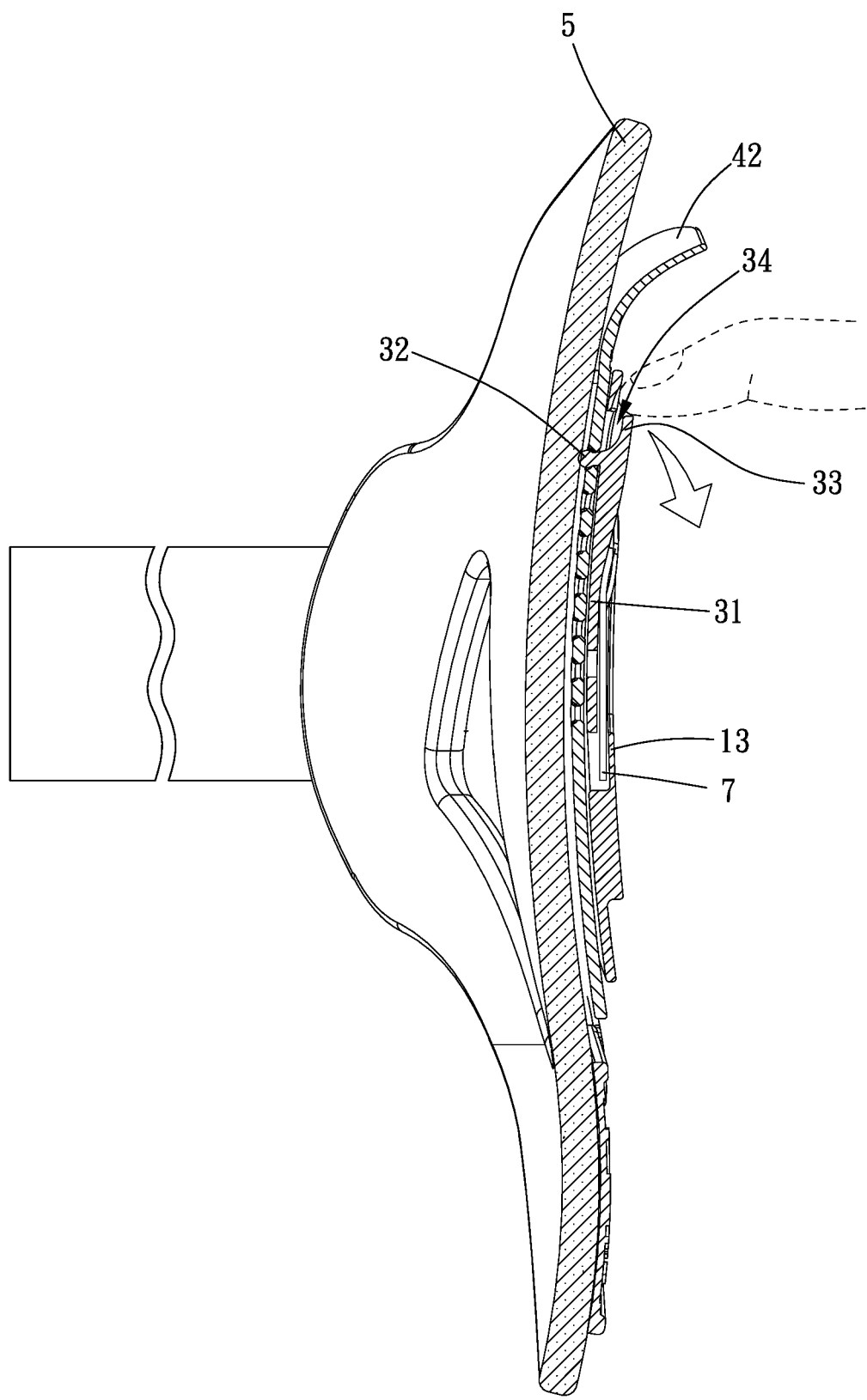
FIGS. 4 and 5 are cross-sectional views of a preferable embodiment of the present invention.
Figure 5:
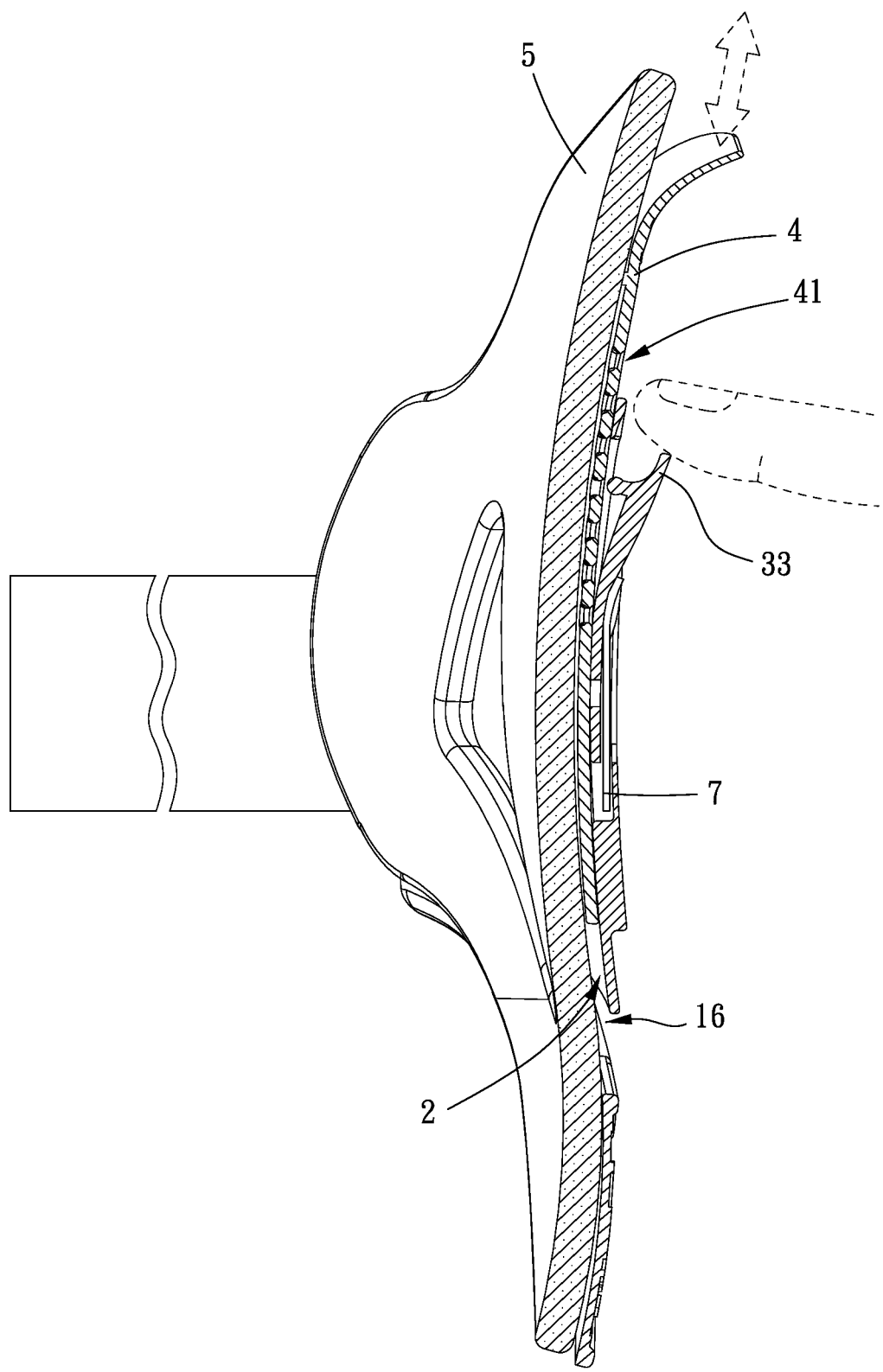
Figure 6:
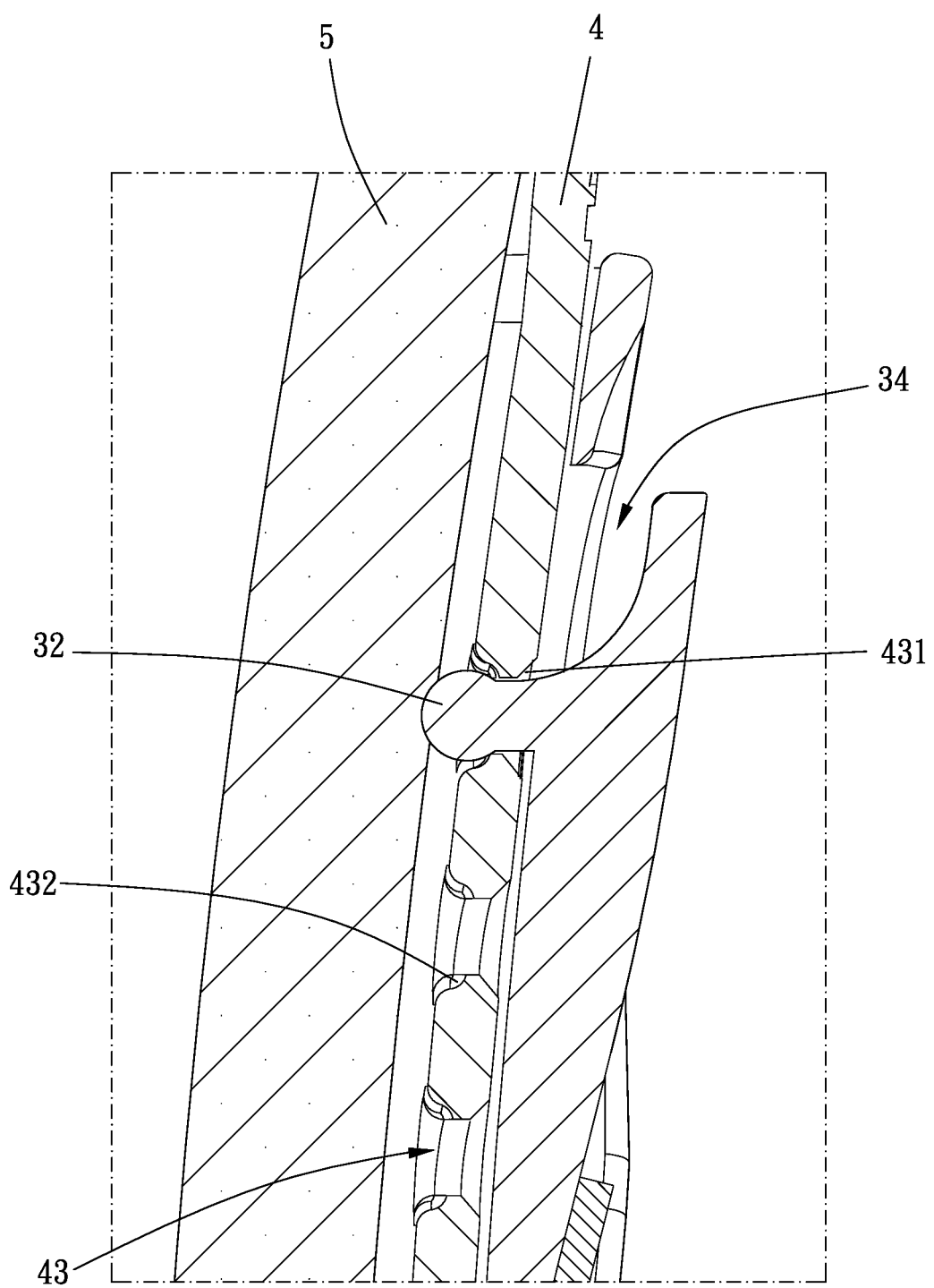
FIG. 6 is a partial enlargement of FIG. 4.
Figure 7:
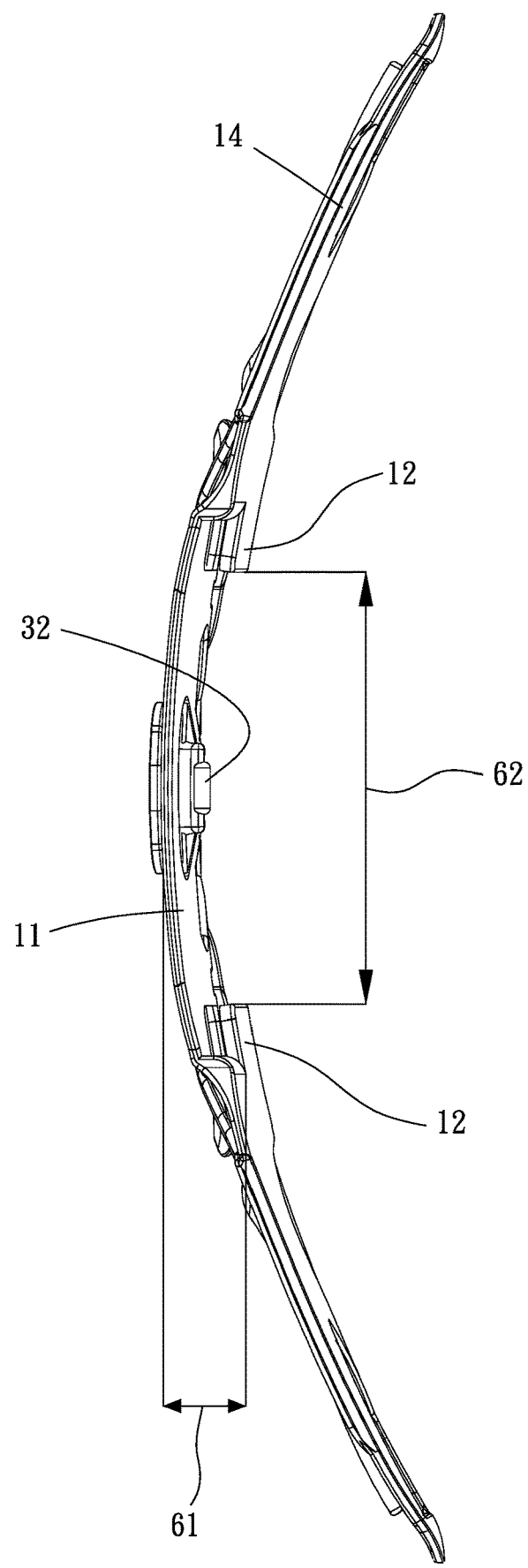
FIG. 7 is a top view of a nape base.
Figure 8:
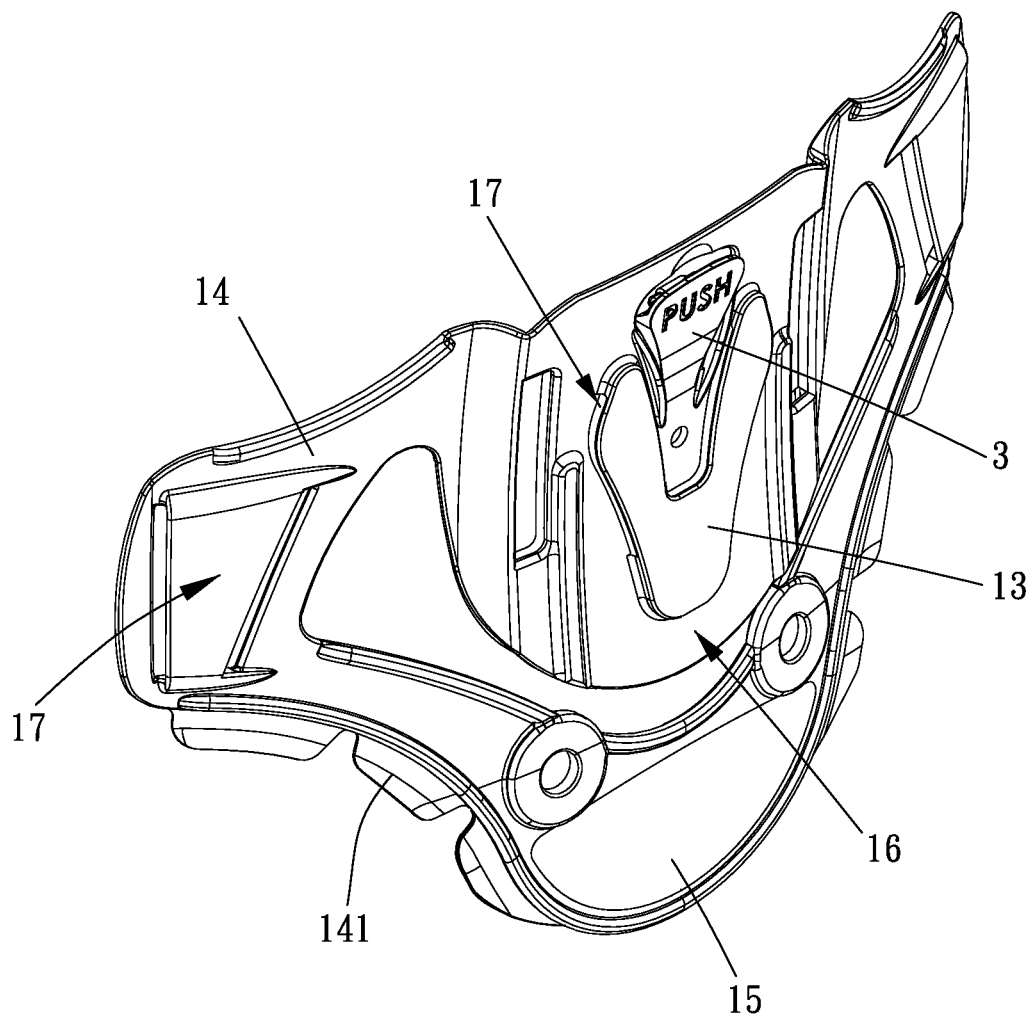
FIG. 8 is a stereogram of a nape base.

Please refer to FIGS. 1 to 8 for a preferable embodiment of the present invention. A rear sheet adjustment assembly of neck collar of the present invention includes a nape base 1 and a support sheet 4.

The nape base 1 includes a main body 11, at least one stopper 12, a positioning member 3 and a plurality of openings 17. The at least one stopper 12 is connected with the main body 11 and defines a first distance 61 and an inserting space 2. For example but not limitation, in this embodiment, a number of the at least one stopper 12 is two and a second distance 62 is defined between the two stoppers 12. The positioning member 3 is disposed between the two stoppers 12. Moreover, the second distance 62 is at least four times the first distance 61. The positioning member 3 and the at least one stopper 12 are disposed oppositely on the main body 11, and at least part of the positioning member 3 is movable to a blocking position or a releasing position. A first combination portion 32 of the positioning member 3 is insertable into the inserting space 2 when changing in position. Each of the openings 17 is configured for a band 7 to be disposed therethrough.

The support sheet 4 is configured to support a nape and be movably inserted within the inserting space 2. The support sheet 4 includes a plurality of second combination portions 41, and each of the second combination portions 41 is adjustably engageable with the first combination portion 32.

The first combination portion 32 is located at the inserting space 2 and engaged with one of the second combination portions 41 when the positioning member 3 is in the blocking position. The first combination portion 32 is departed from the second combination portions 41 and moved away from the support sheet 4 when the positioning member 3 is in the releasing position.

The support sheet 4 is slidably adjusted relative to the nape base 1 according to different neck lengths of users so that the user's head is perfectly supported and restricted to prevent the head from excessive swinging, shaking or leaning backwards and being hurt again. Moreover, adjustment of the support sheet 4 can be contingent upon rehabilitation of the user's neck to increase the extent of neck movement step by step.

Preferably, the nape base 1 further includes two wing portions 14 which are oppositely connected with the main body 11 and a leaning portion 15. Each of the wing portions 14 is configured to cover lateral side of the neck portion of the human in order to obtain better protection effect. When the nape base 1 is worn on the nape, the leaning portion 15 is configured to be abutted against the back of the human body so that the nape base 1 can be reliably and stably positioned on the nape of the neck. Moreover, each of the wing portions 14 has a plurality of attaching portions 141 which extend outwardly, and each of the attaching portions 141 is configured to be attached to the back or the shoulder of the human body to increase a contact area between the nape base 1 and the human body and improve stability. Specifically, each of the wing portions 14 has at least one of the openings 17 which allows the band 7 to be disposed therethrough and be connected firmly with a front neck base.

An aperture 16 is disposed on the nape base 1, and an extending path of the aperture 16 extends from one of the wing portions 14 through an intermediate between the main body 11 and the leaning portion 15 and into the other one of the wing portions 14. With the aperture 16, the structure of the nape base 1 is easy to be bent and deformed to apply widely to different figures of the users. Moreover, the aperture 16 is communicated with the inserting space 2 so that outside air is easy to enter the inserting space 2 to keep validated and prevent the skin of the nape from discomfort due to long-term coverage. Preferably, the aperture 16 is boomerang-shaped.

In this embodiment, the nape base 1 and the support sheet 4 are made of flexible elastic materials so that they have good flexibility and can be closely attached to different shape of the nape to perfectly support and protect the nape. Moreover, the support sheet 4 further preferably includes an arc portion 42, and the arc portion 42 is configured to support back of the head to restrict the user's head and prevent the head and the neck from getting injured again due to unnecessary movement.

Furthermore, the positioning member 3 further includes a base portion 31 which is connected with the main body 11, and the base portion 31 is made of a flexible elastic material. The first combination portion 32 is disposed on the base portion 31. When being stressed by an external force, the base portion 31 is bent relative to the main body 11 and the first combination portion 32 is moved away from the support sheet 4; when being unstressed, the base portion 31 elastically recovers and the first combination portion 32 moves toward the support sheet 4.

Specifically, the main body 11 has a restricting portion 13 on a side facing away from the support sheet 4, and the restricting portion 13 is v-shaped. A sidewall of the restricting portion 13 has two of the openings 17 disposed therethrough which are communicated with the inserting space 2. The base portion 31 and the main body 11 are formed integrally and a part of the base portion 31 is located at an interval of the restricting portion 13 and their outlines are complementary. Therefore, a part of the band 7 in the inserting space 2 is disposed between the base portion 31 and the restricting portion 13 so as to restrict the band 7 effectively.

In this embodiment, the first combination portion 32 is a projection and each of the second combination portions 41 is a hole. The projection is disposed within and engaged with the hole so that the support sheet 4 is positioned and unable to be moved randomly.

Preferably, each of the holes is defined by a circumferential wall 43 which includes an inclined portion 431 facing the positioning member 3. An extending direction of the inclined portion 431 is oblique to an opening direction of the hole so that the projection is slidably abutted against the inclined portion 431 and inserted into the hole to achieve rapid combination.

Moreover, the hole penetrates the support sheet 4, and the circumferential wall 43 further includes an engaging portion 432 which faces away from the positioning member 3. The engaging portion 432 is stepped. When the projection is disposed within the hole, the projection is interfered with the engaging portion 432 in the opening direction of the hole to form a stable combination structure so that the first combination portion 32 may not depart from the second combination portions 41 due to unexpected external forces. In addition, a position of the support sheet 4 must to be adjusted for different requirements so that the projection is cylindrical and its axial direction is transverse to the opening direction of the hole to allow the user to smoothly pull the first combination portion 32 out of the second combination portions 41.

The positioning member 3 further includes a pull portion 33. The pull portion 33 is protuberantly connected with the base portion 31 and defines an interval 34 with the main body 11. The interval 34 is configured for insertion of a finger so that the user can bend and move the positioning member 3 to the releasing position. Specifically, the first combination portion 32 is preferably disposed adjacent to the pull portion 33 so that a small range of bending is needed to rapidly switch to the blocking position or the releasing position.

The rear sheet adjustment assembly of neck collar further includes a flexible cushion member 5. The flexible cushion member 5 is disposed on the support sheet 4 and configured to be abutted against the head and neck of a human body to have better wearing comfortability. It is understandable that an area of the flexible cushion member 5 is larger than an area of the support sheet 4.

In summary, the rear sheet adjustment assembly of neck collar emphasizes wide applicability. The support sheet is slidable and positionable relative to the nape base to apply to the neck of different users, and the support sheet can perfectly support and protect the neck to prevent the neck from getting injured again due to unexpected movement.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A rear sheet adjustment assembly of a neck collar, including:
a nape base, including a main body, at least one stopper, a positioning member and a plurality of openings, the at least one stopper being connected with the main body and defining a first distance and an inserting space therebetween, the positioning member and the at least one stopper being disposed oppositely on the main body, at least part of the positioning member being movable to a blocking position or a releasing position, a first combination portion of the positioning member being insertable into the inserting space when changing position, each opening of the plurality of openings being configured for a band to be disposed therethrough;
a support sheet, being configured to support a nape, being movably inserted within the inserting space, including a plurality of second combination portions, each of the plurality of second combination portions being adjustably engageable with the first combination portion;
wherein the first combination portion is located at the inserting space and engaged with one of the plurality of second combination portions when the positioning member is in the blocking position; the first combination portion is departed from the plurality of second combination portions and moved away from the support sheet when the positioning member is in the releasing position; and wherein the first combination portion is a projection, each of the plurality of second combination portions is a hole, and the projection is disposed within and engaged with the hole, wherein each hole is defined by a circumferential wall which includes an inclined portion facing the positioning member, and an extending direction of the inclined portion is oblique to an opening direction of the hole; and wherein the hole penetrates the support sheet, the circumferential wall further includes an engaging portion which faces away from the positioning member, the engaging portion is stepped, and when the projection is disposed within the hole, the engaging portion interferes with the projection in the opening direction of the hole.

2. The rear sheet adjustment assembly of the neck collar of claim 1, wherein the positioning member further includes a base portion which is connected with the main body, the base portion is made of a flexible elastic material, the first combination portion is disposed on the base portion; when being stressed by an external force, the base portion is bent relative to the main body and the first combination portion is moved away from the support sheet; when being unstressed, the base portion elastically recovers and the first combination portion moves toward the support sheet.

3. The rear sheet adjustment assembly of the neck collar of claim 2, wherein the positioning member further includes a pull portion, the pull portion is protuberantly connected with the base portion and defines an interval with the main body, and the interval is configured for insertion of a finger.

4. The rear sheet adjustment assembly of the neck collar of claim 3, wherein the main body has a restricting portion on a side facing away from the support sheet, a sidewall of the restricting portion has two of the plurality of openings disposed therethrough which are communicated with the inserting space; the at least one stopper comprises two stoppers, a second distance is defined between the two stoppers, and the positioning member is disposed between the two stoppers; the rear sheet adjustment assembly of the neck collar further includes a flexible cushion member, and the flexible cushion member is disposed on the support sheet and configured to be abutted against a head and neck of a human body; the second distance is at least four times the first distance; the support sheet further includes an arc portion, the arc portion is configured to support a back of the head; the nape base and the support sheet are made of flexible elastic materials; the base portion and the main body are formed integrally; the first combination portion is disposed adjacent to the pull portion; the projection is cylindrical and an axial direction of the projection is transverse to the opening direction of the hole; the restricting portion is v-shaped, a part of the base portion is located at an interval of the restricting portion and their outlines are complementary, a part of the band in the inserting space is disposed between the base portion and the restricting portion; the nape base further includes two wing portions which are oppositely connected with the main body and a leaning portion, each of the wing portions is configured to cover a lateral side of a neck portion of a human, each of the wing portions has at least one of the plurality of openings, the leaning portion is configured to be abutted against a back of the human body; an aperture is disposed on the nape base, an extending path of the aperture extends from one of the wing portions through an intermediate between the main body and the leaning portion and into another one of the wing portions, the aperture is boomerang-shaped; the aperture is communicated with the inserting space; an area of the flexible cushion member is larger than an area of the support sheet; each of the wing portions has a plurality of attaching portions which extend outwardly, and each of the plurality of attaching portions is configured to be attached to the back or a shoulder of the human body.

5. The rear sheet adjustment assembly of the neck collar of claim 1, wherein the main body has a restricting portion on a side facing away from the support sheet, a sidewall of the restricting portion has two of the plurality of openings disposed therethrough which are communicated with the inserting space.

6. The rear sheet adjustment assembly of the neck collar of claim 1, wherein the at least one stopper comprises two stoppers, a second distance is defined between the two stoppers, and the positioning member is disposed between the two stoppers.

7. The rear sheet adjustment assembly of the neck collar of claim 1, further including a flexible cushion member, wherein the flexible cushion member is disposed on the support sheet and configured to be abutted against a head and neck of a human body.

* * * * *